(12) United States Patent
John et al.

(10) Patent No.: US 10,851,348 B2
(45) Date of Patent: Dec. 1, 2020

(54) PROLIFERATIVE PRIMARY HUMAN SERTOLI CELL CULTURES AND THEIR APPLICATIONS

(71) Applicant: Mandalmed, Inc., San Francisco, CA (US)

(72) Inventors: Constance M. John, San Francisco, CA (US); Alpa Mahuvakar, Union City, CA (US)

(73) Assignee: MANDALMED, INC., San Francisco, CA (US)

(*) Notice: Subject to any disclaimer, the term of this patent is extended or adjusted under 35 U.S.C. 154(b) by 93 days.

(21) Appl. No.: 15/277,919

(22) Filed: Sep. 27, 2016

(65) Prior Publication Data

US 2017/0114327 A1   Apr. 27, 2017

Related U.S. Application Data

(63) Continuation of application No. 12/090,063, filed as application No. PCT/US2007/002152 on Jan. 26, 2007, now abandoned.

(60) Provisional application No. 60/762,949, filed on Jan. 26, 2006.

(51) Int. Cl.
   *C12N 5/071* (2010.01)
   *A61K 35/48* (2015.01)

(52) U.S. Cl.
   CPC ........... *C12N 5/0683* (2013.01); *A61K 35/48* (2013.01); *C12N 2501/31* (2013.01); *C12N 2502/246* (2013.01); *C12N 2503/00* (2013.01); *C12N 2510/00* (2013.01)

(58) Field of Classification Search
   None
   See application file for complete search history.

(56) References Cited

U.S. PATENT DOCUMENTS 5,585,265 A * 12/1996 Kahn ................... C12N 5/0621
                                                        435/320.1

OTHER PUBLICATIONS

Sharpe et al. Proliferation and functional maturation of Sertoli cells, and their relevance to disorders of testis function in adulthood. Reproduction. Jun. 2003;125(6):769-84.*

Lejeune et al. Enhancement of testosterone secretion by normal adult human Leydig cells by co-culture with enriched preparations of normal adult human Sertoli cells. Int J Androl. Feb. 1993;16(1):27-34.*

Mather. Establishment and characterization of two distinct mouse testicular epithelial cell lines. Biol. Reprod. Aug. 1980;23(1):243-52.*

Ahmed et al. Proliferative activity in vitro and DNA repair indicate that adult mouse and human Sertoli cells are not terminally differentiated, quiescent cells. Biol Reprod. Jun. 2009;80(6):1084-91. Epub Jan. 21, 2009.*

Chui et al. Characterization and functionality of proliferative human Sertoli cells. Cell Transplant. 2011;20(5):619-35. Epub Nov. 5, 2010.*

Buzzard et al. Marked extension of proliferation of rat Sertoli cells in culture using recombinant human FSH. Reproduction. Nov. 2002;124(5):633-41.*

Schlatt et al., Biol. Reprod. 1996, 55:227-235.*

* cited by examiner

*Primary Examiner* — James D Schultz
(74) *Attorney, Agent, or Firm* — Ann-Louise Kerner

(57) ABSTRACT

Technology for the isolation and propagation of primary human Sertoli cells from normal testes tissue, including cultures of proliferative primary human Sertoli cells for research and clinical applications, and a pharmaceutical composition for cell therapy, ex vivo gene therapy, and for the reduction of autoimmune, allograft, and xenograft immune reactions.

4 Claims, 10 Drawing Sheets

PROLIFERATIVE PRIMARY HUMAN SERTOLI CELL CULTURES AND THEIR APPLICATIONS

TECHNICAL FIELD

The Sertoli cell creates the blood-testis barrier in the seminiferous tubules of the testes, and is critical for the production of viable, haploid sperm. Sertoli cells are among several types of cells that have specialized capability to ward off the immune system and that therefore have been termed "immune-privileged". Sertoli cells also have other characteristics that make them potentially valuable for various types of dell therapies. The present invention consists of technology for the isolation of proliferative Sertoli cells from human testis tissue and for their propagation for applications in cell and gene therapy and for research in reproductive health and other areas. Using this technology, human Sertoli cell that have the ability to proliferate in cell culture can be isolated from testis tissue, and can be frozen, thawed and continue to proliferate upon further culture after thawing. The method described enables the isolation of primary human Sertoli cells that can be propagated in vitro from cadaveric or other sources of normal testis tissue. Allo- or xenogeneic implants of various types of non-human mammalian Sertoli cells have shown benefit in vivo in co-transplantation to protect implants of other types of cells, such as beta islet cells, from immune rejection, for use in ex vivo gene therapy, for infertility due to a deficiency of Sertoli cells, and as therapy in models of Parkinson's and other neurodegenerative diseases.

BACKGROUND ART

The Sertoli cell (Enrico Sertoli, 1842-1910, an Italian histologist) is a sustentacular cell that can be identified in hematoxylin and eosin preparations by its nucleus. It is described as a "nurse" cell that sustains the environment for the developing spermatozoa. The Sertoli cell maintains the "blood-testis" barrier (BTB) by forming occluding junctions that separate the tubules that comprise the seminiferous epithelium into two compartments. The inner, apical compartment is isolated from blood borne elements to protect the sperm from potential damaging autoimmune reactions because its haploid nature can create immunologic recognition as "non-self". Sertoli cells produce nutrients to nourish the developing sperm, and cell stimulatory factors that stimulate cell proliferation and maturation, help protect sperm against various toxins, and participate in hormonal regulation of spermatogenesis. In the fetus, Sertoli cells are thought to direct the development and descent of the testes, and to have an important role overall in maintenance of male fertility because each Sertoli cell nurtures a fixed number of germ cell clones by supplying nutrients and growth factors during their 10 week maturation period. Therefore, the fewer Sertoli cells that ultimately form, the smaller the testes will be and the fewer the number of sperm that can be produced.

Because of their special characteristics, many laboratories have studied the nature of Sertoli cells and the activity of both human Sertoli cells and Sertoli cells from other mammalian specie. Investigations have shown that Sertoli cells can provide support for other types of cells in vitro such as neuronal progenitors (McGrogan and Snable 2002) and the beta islets of the pancreas (Luca, Nastruzzi et al. 2005; Teng, Xue et al. 2005) that produce insulin, and cryopreserved cells In addition, there have been many reports of therapeutic effects of Sertoli cells in animal disease models—primarily using allogeneic Sertoli cells but also in some cases xenogeneic cells. Sertoli cells are particularly attractive for cell-based therapy because with these cells allogeneic implantation is a possibility with no or with reduced amounts of immunosuppression.

Primary Sertoli cells from rodents have been shown to act as cytoprotective "nurse" cells or to prevent allograft, xenograft, or autoimmune reactions in animal models of diseases such as Parkinson's and other neurodegenerative diseases (Sanberg, Borlongan et al. 1996; Sanberg, Cameron et al. 1995; Sanberg, Cameron et al. 1995; Willing, Sudberry et al. 1999; Sanberg, Cameron et al. 1996; Cameron, Hushen et al. 2001), diabetes (Selawry and Cameron 1993; Selawry 1995; Korbutt, Elliott et al. 1997; Selawry 1998; Selawry 1999; Selawry 2000; Suarez-Pinzon, Korbutt et al. 2000; Dufour. Rajotte et al. 2003; Dufour, Halberstadt et al. 2005); amyotrophic lateral sclerosis (Hemendinger, Wang et al. 2005), and Huntington's disease (Rodriguez, Willing et al. 2003). Recent data indicates that including peritubular myoid cells of the testes with the Sertoli cells increases their ability to suppress graft rejection (Dufour, Halberstadt et al. 2005). We showed that genetically modified allogeneic Sertoli cells secreted recombinant protein and suppressed inflammation in a rat contusion model of spinal cord injury (Trivedi, Igarashi et al. 2006).

Sertoli cells potentially could have applications in facilitation of transplantation of pancreatic islet cells in type 1 diabetes (Halberstadt, Emerich et al. 2004). Although using the Edmonton protocol for islet transplantation in subjects with type 1 diabetes mellitus can restore endogenous insulin production (Shapiro, Lakey et al. 2000; Ryan, Lakey et al. 2001; Shapiro, Ricordi et al. 2006), it was not sustained in the majority even with long-term immunosuppression that can have debilitating side effects. Only 5 of 36 Islet recipients were still insulin independent after two years (Shapiro, Ricordi et al. 2006). One approach that has been used successfully in animals is the transplantation of allogeneic Sertoli cells along with beta islets (Selawry and Cameron 1993; Korbutt, Elliott et al. 1997; Suarez-Pinzon, Korbutt et al. 2000; Dufour, Rajotte et al. 2003). In one of the first studies in this area allogeneic beta islets survived more than 50 days in diabetic rats with no adjuvant immunosuppression when implanted in testes that were surgically placed in the abdomen (Selawry and Whittington 1984). In the non-obese diabetic (NOD) mouse model of type 1 diabetes it was shown that the implantation of syngeneic Sertoli cells and beta islets under the capsule of opposing kidneys produced normoglycemia in the majority of animals for more than 60 days (Suarez-Pinzon, Korbutt et al. 2000). This data indicates that Sertoli cells can produce systemic immunosuppression in addition to localized effects.

In a study of xenogeneic grafts, neonatal porcine Sertoli cells survived in the kidney capsule of nonimmunosuppressed rats for up to 40 days (Dufour, Rajotte et al. 2003). Positive results were reported in half of the subjects of a recent controversial trial that tested the survival of porcine Sertoli cells and islets in 12 nonimmunosuppressed human type 1 diabetics (Check 2002; Valdes-Gonzalez, Dorantes et al. 2005).

However, neonatal porcine Sertoli cells did not protect porcine islets from immune rejection in nonimmunosuppressed diabetic rats (Wang, Skinner et al. 2005). It could be advantageous for prevention of immune rejection and autoimmunity to use human (allogeneic) rather than Sertoli cells from pigs or other mammals (xenogeneic) to protect beta islets or other cells. But a ready supply of primary human Sertoli cells has not been available previously.

In cell therapy, perhaps the most exciting developments are based on the discoveries in stem cells that have ability to terminally differentiate into various types of cells. Embryonic stem cells from the inner cell mass of a blastocyst can differentiate into any cell type found in the body, such as beta islet cells from the pancreas or neurons. Stem cells have potentially enormous application in treatment of disease. One of the significant hurdles in their application is that according to some reports allogeneic embryonic stem cells will be subject to immune rejection when differentiated (Ponsaerts, van Tendeloo et al. 2004; Kofidis, deBruin et al. 2005; Swijnenburg, Tanaka et al. 2005; Grinnemo, Kumagai-Braesch et al. 2006). Mesenchymal-stem cells are thought to be immune-privileged (Krampera, Glennie et al. 2003; Inoue, Popp et al. 2006) but in some circumstances can induce allograft rejection (Nauta, Westerhuis et al. 2006). The availability of a plentiful source of primary human cells that could be co-implanted with allogeneic stem cells and help protect them from immune rejection could be important.

Cultures of human Sertoli cells that proliferate in vitro have not been previously reported. However, it is known that production of Sertoli cells continues after birth. Studies in primates with suppression of follicle stimulating hormone (FSH) in the neonatal period revealed that deficiencies in Sertoli cells observed at the end of the neonatal period were restored by adulthood. Thus it has been assumed that Sertoli cell proliferation can occur during the peripubertal period (Sharpe, McKinnell et al. 2003). But in general it has been thought that past puberty the Sertoli cell number is not changed and that the cells do not proliferate past the peripubertal period or if they do it is in a very limited fashion.

Molecules that have been found to be expressed in Sertoli cells during the neonatal period and beyond include follicle stimulating hormone receptor (FSHr), GATA-4 (Ketola, Pentikainen et al. 2000), and Wilms' tumor gene (WT1) (Sharpe, McKinnell et al. 2003). The gene for the anti-Mullerian hormone is switched on after the differentiation of the Sertoli cells during fetal development and the expression continues until puberty when it is down regulated coincidentally with the final maturation of the Sertoli cells.

Lack of availability of primary human Sertoli cells has limited the opportunity to study their characteristics and functionality, and to develop human Sertoli-cell based cell therapies and co-transplantation protocols. A distinct advantage of using primary rather than transformed cells for cell therapy is that there is less danger of malignancy arising in vivo.

While the isolation and culture of primary human Sertoli cells has been previously described (Lipshultz, Murthy et al. 1982; Lejeune, Sanchez et al. 1998; Teng, Xue et al. 2005) apparently the proliferation of the cells was minimal. The lifespan of the cell cultures was reported to be limited to 32 (Lejeune; Sanchez et al. 1998) and 45 days (Lipshultz, Murthy et al. 1982).

There have been a number of laboratories that have reported the therapeutic benefits of therapy with allogeneic or even xenogeneic Sertoli cells for various disorders or diseases. However, the prior art is deficient in teaching a method or providing a source of human Sertoli cells that proliferate in culture and that therefore could serve as a source of Sertoli cells for various types of clinical applications and for analysis of the function and characteristics of human Sertoli cells.

Animal testing is well established in assessment of human male reproductive toxicity during drug development, and various animal models including genetic knockouts in mice of spermatogenesis have been valuable to our understanding of the process in humans (Escalier 2006). Nonetheless, a number of significant differences between species have been documented including variation in the timing of Sertoli cell proliferation, the effects of androgen suppression, seasonal variability, relative numbers of sperm, and the responses to toxins (Brown, Spielmann et al. 1994; Apostoli, Kiss et al. 1998; Young and Nelson 2001; Sharpe, McKinnell et al. 2003).

Sertoli cell proliferation is thought to occur in two periods in all species, one during fetal and neonatal life, and a second in the peripubertal period. However, in some species, one period is most important, such as in rhesus monkeys where the proliferation mainly occurs in the peripubertal period and in the rat where proliferation in the neonatal period that overlaps with the peripubertal period in time, predominates. Both periods are important in humans where they are separated by more than a decade (Sharpe, McKinnell et al. 2003).

In some animals but not humans, breeding is restricted to certain times of year when reproductive success is most likely. In males depending on the species, there can be a decrease in testicular size from 10-95% during the non-breeding season depending on environmental signals (Young and Nelson 2001). The decrease in size can be correlated with increased testicular apoptosis. Gonadal regression to an immature state is thought to be a reliable method of male reproductive inhibition. In addition, there are variations in the sensitivity of species to suppression of gonadotropin and follicle stimulating hormone (FSH) (Sharpe, McKinnell et al. 2003).

Large differences exist between animals and humans in the relative numbers of sperm. There is typically only two-fold to four-fold higher number of sperm per ejaculate in the human male than that which will be maximally fertile whereas in rats or rabbits the number is up to 1,440 higher (reviewed in (Brown, Spielmann et al. 1994)).

A systematic literature review of studies of the effect of lead exposure on male reproduction found that it was unlikely that valid conclusions could be extrapolated from animal to human data (Apostoli, Kiss et al. 1998). The human studies were primarily focused on semen quality, endocrine function, and birth rates in exposed subjects revealed that concentrations of Inorganic lead>40 µg/dl in blood impaired male reproductive function by reducing total number of sperm count, volume, and density, or altering its motility and morphology. However, in animals certain species and strains showed resistance to the toxic effects of lead that were thought likely due to differences in reproductive end points and in the level of exposure (Apostoli, Kiss et al. 1998).

Abnormalities in Sertoli cell differentiation are thought to be important in the pathophysiology of low sperm count (Carlsen, Giwercman et al. 1993; Swan, Elkin et al. 2000; Skakkebaek, Rajpert-De Meyts et al. 2001) and testicular cancer (Petersen and Soder 2006), that have been increasing in several Western countries in recent decades. The concentration of sperm and the volume of semen in Western countries declined significantly between 1930 and 1991 (Carlsen. Giwercman et al. 1993; Swan, Elkin et al. 2000; Skakkebaek, Rajpert-De Meyts et al. 2001). Among the postulated causes for declining semen quality are chemical and pesticide exposure (Swan, Kruse et al. 2003; Fisher 2004).

The correlation of animal with human male reproductive toxicity is not always accurate and is less likely to be so during development (Brent 2004). Threshold exposures, maximum permissible exposures, and toxic effects can be estimated from animals but epidemiological studies are still considered by some as the best means of assessing human risk (Brent 2004). There is an unmet need for better, alternative methods for safety testing of drugs; chemicals and cosmetics (Hareng, Pellizzer et al. 2005). Using human Sertoli cells rather than rat or other mammalian Sertoli cells in a model system for male reproductive toxicity and safety testing should produce results that more accurately reflect human sensitivity.

Development of an effective, consumer-friendly contraceptive for men remains challenging (Matthiesson and McLachlan 2006). The three most established approaches to male contraception are (1) the barrier method such as the condom, (2) hormonal treatments that can disrupt the pituitary-testicular axis and prevent spermatogenesis, and (3) immune methods using vaccines targeted to specific male antigens (Cheng, Silvestrini et al. 2001). An alternative approach has been developed in which attachments of developing germ cells onto the Sertoli cells in the seminiferous epithelium are disrupted, thereby inducing their premature release into the tubular lumen (Chung, Lee et al. 1999; Cheng, Silvestrini et al. 2001; Cheng, Mruk et al. 2005) producing infertility. Development of an in vitro model of human spermatogenesis using human Sertoli and germ cells would enable better understanding of the regulation of the three types of junctions that are found in the testis (1) occluding or tight, (2) anchoring or adhering, and (3) communicating or gap (reviewed in (Cheng and Mruk 2002). This could lead to the discovery of new targets for non-hormonal male contraceptive development (Wenk and Nieschlag 2006).

Approximately one in six couples worldwide are afflicted by unwanted childlessness that can be attributed to the male in 20% of the cases, and to both the male and female in 15%. The incidence of male infertility is approximately 7% (Brehm and Steger 2005). No specific cause can be identified for the majority of infertile men. Infertility in men can be secondary to testicular germ cell cancer that may be facilitated by altered maturation of Sertoli cells or aberrant Sertoli cell-germ cell communication. (Brehm and Steger 2005).

Infertility due to testicular atrophy and azoospermia also are common adverse effects of cancer treatments (Schrader, Heicappell et al. 2001; Boekelheide 2005; Howell and Shalet 2005). Animal experiments have implicated the Fas system and Sertoli cells in germ cell apoptosis form mono-(2-ethylhexyl)phthalate (MEHP) supporting a role for Fas and p53 in regulating testicular responses to insults (reviewed in (Boekelheide 2005)). Changes in the structure and function of Sertoli cells after cisplatin exposure indicate that the inter-Sertoli cell junctions of the BTB become leaky causing alteration in seminiferous tubule fluid electrolytes and decrease in androgen binding protein levels (Boekelheide 2005).

Sertoli cells isolated from testes of donor male mice were injected into the testes of infertile murine recipients where they were able to support spermatogenesis (Shinohara, Orwig et al. 2003). These data indicate that allogeneic Sertoli cells could be therapeutic for those males that are infertile because they have too few or defective Sertoli cells. In addition, better understanding of the biology of the human testes and particularly human Sertoli cells could increase our knowledge about the causes of and new ways to treat male infertility.

SUMMARY OF THE INVENTION

The present invention relates to the surprising discovery of methodology enabling the isolation of a small number of primary Sertoli cells from adult human testicular tissue that proliferate and can be passaged in vitro enabling expansion of the population. With this methodology, few Sertoli cells are detected adhering to the culture dish even 2-10 days post-isolation and, thus, the isolated cells must represent only a small percentage of the Sertoli cells in the testes that in adult men that number approximately 4 billion (Johnson, Zane et al. 1984; Cortes, Muller et al. 1987). Despite the isolation of only a few viable primary Sertoli cells, these proliferate until becoming confluent. The population can be greatly expanded by continuously passaging the cells for months such that the Sertoli cells that can be produced from a single donor are more than would be expected to be obtained originally from 10-20 individuals. This technology enables for the first time the production of a large number of primary human Sertoli cells from a single donor that will be suitable for a number of research and therapeutic applications.

In a preferred embodiment, the proliferative Sertoli cells are administered for treatment of a disease by the prevention of immune rejection of co-implanted cells, such as beta islet cells that produce a biological factor such as insulin that is lacking in the disease.

In another aspect of the invention, the proliferative Sertoli cells are used to nourish, or stimulate the proliferation or differentiation of other cells by co-culturing the cells in vitro with Sertoli cells or by using conditioned media from Sertoli cells.

In a further aspect of the invention the proliferative human Sertoli cells are administered to a site in the body where they can nourish; or stimulation the proliferation or differentiation of other cells, such as neurons, for treatment of various conditions or diseases, such as Parkinson's disease or stroke.

In a preferred embodiment, the Sertoli cells are used for ex vivo gene therapy of a disease or condition. Thus, the Sertoli cells are genetically modified to produce and secrete a recombinant protein, peptide, or glycoprotein and then administered so that the recombinant molecule is delivered in the body.

In one embodiment, the Sertoli cells are administered to the testes for treatment of male infertility resulting from lack of, or disorders of Sertoli cells.

In another embodiment the Sertoli cells are used in the study of normal or abnormal physiology, and in analysis of male reproductive toxicology.

In a preferred embodiment, polarized Sertoli cells are used in a model system with other testicular cells such as germ and Leydig cells for research and development of male contraceptive molecules, and in models of human spermatogenesis. In another embodiment, polarized Sertoli cells are used to create a model of the blood-testis barrier (BTB) for the analysis of the toxicity of compounds for the testis and for determining the distribution of compounds or drugs across the BTB.

DESCRIPTION OF THE DRAWINGS

FIG. 1A is a bright-field photomicrographs of human Sertoli (MM-HSE-2305) cells in culture. FIG. 1B is a 40× magnification of FIG. 1A. FIG. 1C is a bright-field photomicrographs of human Sertoli (MM-HSE-2305) cells in culture. FIG. 1D is a 200× magnification of FIG. 1C.

DETAILED DESCRIPTION OF THE PREFERRED EMBODIMENTS OF THE INVENTION

Definitions

Figure 1:
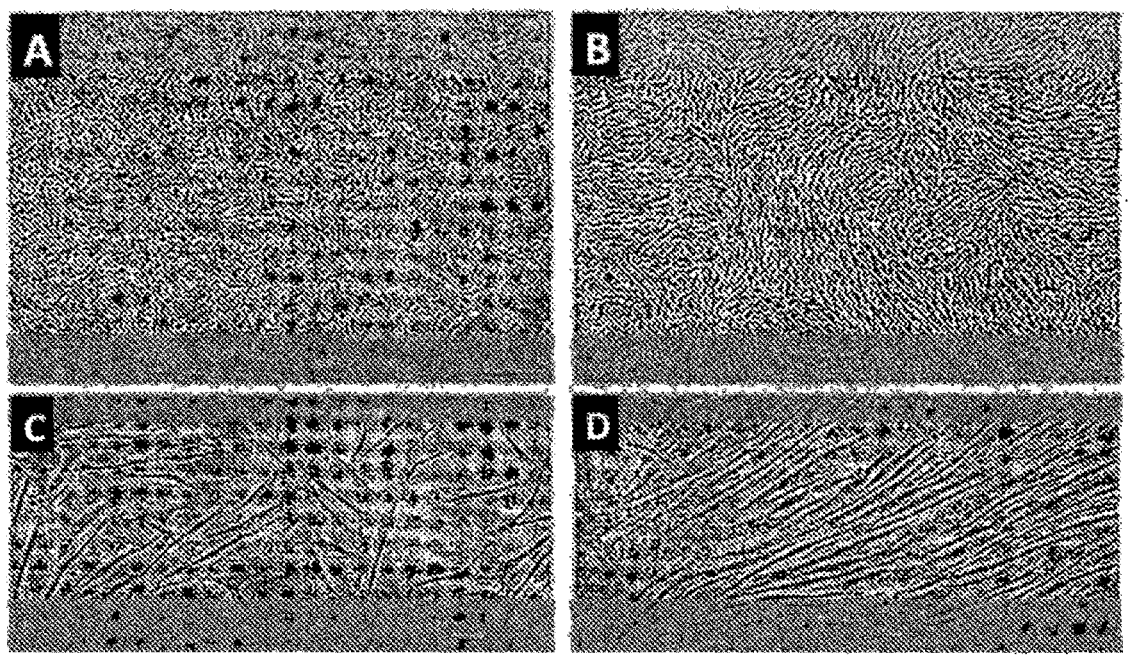

The term "administer" means to apply as a remedy. There are different methods that have been and can be used to administer cells as a remedy. For example, the cells can be surgically implanted, infused or injected subcutaneously, intravenously, Intramuscularly, or intraperitoneally or within a particular site or organ of the body, or placed in a device that is implanted.

The term "ex vivo gene therapy" normally refers to autologous ex vivo gene therapy in which a patient's own cells are collected and cultured in the laboratory. The new gene is incorporated into the growing cells, and these are subsequently transferred back into the patient. In the context of this invention, "ex vivo gene therapy" refers to the use of cultured allogeneic Sertoli cells into which a new gene is incorporated. The genetically modified allogeneic Sertoli cells are transferred into the patient where they can deliver the gene product.

The term "polarized" refers to the characteristic feature of polarized cells that is the division of their surface into functionally distinct membrane domain. Many of the cells of multicellular organisms are polarized. Epithelial cells are prototypical polarized cells. Epithelial cells form a protective barrier against the external environment, and serve as exchange interfaces with the outside world. To do this, epithelial cells have evolved characteristic apical and basolateral membrane domains. The basolateral membrane contacts the neighboring cells and underlying tissue. The apical membrane faces the lumen of an internal organ, and these two domains are separated by tight junctions. The tight junctions seal the epithelium. Polarized Sertoli cells separate the seminiferous epithelium into basal and adluminal compartments. The inner, apical compartment is isolated from blood borne elements to protect the sperm from potential damaging autoimmune reactions.

Preferred Embodiments

The present invention consists of technology to isolate proliferative primary human Sertoli cells, and a method to produce cultures of proliferative primary human Sertoli cells from human testes tissue for various uses in cell or gene therapy, and for research in reproductive health and other areas. The primary human Sertoli cell cultures, are isolated from normal adult donor tissues, have the ability to proliferate in cell culture, and can be frozen, thawed and continue to proliferate upon further culture after thawing. The human Sertoli cells retain their distinctive morphology, express markers characteristic for Sertoli cells, and retain their immunosuppressive ability.

An important advantage of the Sertoli cell cultures is that the cells proliferate readily in culture enabling great expansion of the population. We have observed doubling times of approximately 3-4 days in cultures of earlier passage numbers that are not allowed to become more than approximately 80% confluent. When cultures are allowed to grow until 90-100% confluent, longer doubling times are observed.

The ability to freeze-thaw the cells coupled with their ability to be expanded in culture after thawing—means that the cultures could be maintained for an extended period of time potentially lasting many years if desired. With standard techniques for fluorescence-assisted cell sorting (FACS) or limiting dilution, clonal cultures could be derived from a single cell thereby creating more highly standardized cultures for therapeutic applications.

In a preferred aspect, the cells are useful for slowing the progression of the symptoms of a disease. In another preferred application the cells are useful for reducing the dosage of immunosuppressive drugs required to prevent rejection of co-implanted allogeneic or xenogeneic cells in treatment of a disease or condition.

In another embodiment, the Sertoli cells are useful for helping to prevent the rejection of implanted pancreatic beta islet cells in treatment of type 1 diabetics wherein the Sertoli cells could assist in prevention of autoimmunity, allograft, or xenograft rejection of the islets or to insulin. The human Sertoli cells could be used with islets isolated from cadavers (Shapiro, Lakey et al. 2000; Ryan, Lakey et al. 2001; Shapiro, Ricordi et al. 2006); differentiated from human embryonic stem cells (D'Amour, Bang at al. 2006) or adult stem cells, or with islets from mammals such as pigs (Valdes-Gonzalez, Dorantes et al. 2005). The capability to greatly expand the population of proliferative human Sertoli cells in vitro should enable production of an adequate number of cells for therapeutic applications.

In an early clinical trial of the utility of Sertoli cells to prevent autoimmune and xenograft rejection, pig Sertoli cells and pig beta islets were implanted in 12 human subjects with type 1 diabetes who were followed for a 4-year period. Half of the patients showed a significant reduction in exogenous insulin requirement over this period (Valdes-Gonzalez, Dorantes et al. 2005). The neonatal porcine islets and Sertoli cells were placed in a collagen-generating device implanted subcutaneously in the anterior abdominal wall. Islets and Sertoli cells from ten neonatal pigs were used for each transplant. The collagen-generating devices were implanted and left in place for two months to allow formation of vascularized collagen around the device prior to infusing the cells. There were 250,000 islets implanted along with 30-100 Sertoli cells per islet ($7.5\text{-}25 \times 10^6$ Sertoli cells) and all of the subjects except one had a second implant from 6-9 months later.

In another embodiment, the human Sertoli cells are genetically modified to express and to secrete or produce recombinant protein that is therapeutic in a particular disease or condition. Cell-based or "ex vivo" gene therapy is an alternative to direct injection of viral vectors that can be unable to deliver the desired product due to inability to modify the cells at a particular site or to modify cells of a particular type so as to provide the recombinant protein product where it is needed. This therapy is hindered due to a lack of "off-the-shelf" availability of cells that are well tolerated. One possible alternative is to use immune-privileged cells, like Sertoli cells. In this embodiment, the genetically modified human Sertoli cells are administered allogeneically in the body where they can deliver the recombinant protein to the desired site of action. We have shown that genetically modified rat Sertoli cells are able to secrete recombinant neurotrophin-3 in vitro and in vivo. The genetically modified allogeneic Sertoli cells retained immunosuppressive ability and were able to survive within the inflammatory state of a spinal cord injury model (Trivedi, Igarashi et al. 2006).

In another embodiment, the tumorigenicity of the primary human Sertoli cells can be assessed and compared with cultures of other cells by injection of the cells in suspension subcutaneously in nude mice. After observation for 3 weeks, 5 animals per cell type are deeply anesthetized and sacrificed and the grafted area identified, surgically excised, and the tissue processed for cytological analysis of the implanted cells.

In another embodiment, the proliferative human Sertoli cells can be used in vitro to nourish and support the growth and differentiation of other cells in culture, such as beta islet or stem cells. It has been shown previously that human Sertoli cells could enhance the function of allogeneic islets when they were co-cultured in vitro (Teng, Xue et al. 2005). Murine Sertoli cells facilitated the growth and differentiation of primate embryonic stem cells into dopaminergic neurons (Yue, Cui et al. 2006).

In a preferred embodiment, the proliferative human Sertoli cells are administered to a patient along with terminally differentiated allogeneic or xenogeneic stem cells in cell therapy for replacement of damaged or missing cells. The Sertoli cells help to ward off immune rejection of the allogeneic or xenogeneic stem cells by the host.

Development of cell-based pharmaceutical or tissue products requires establishing a number of process controls that include standardization and optimization of processing procedures and reagents. Acceptance criteria and product characterization protocols must be established to ensure product integrity, and analytical approaches for the evaluation of proposed acceptance criteria must be developed. Product parameters that anticipate adverse events must be identified. Parameters that are evaluated for cells often include morphologic evaluation, detection of phenotype-specific cell surface antigens, unique biochemical markers, gene and protein expression analysis (microarray and proteomics), cellular impurities profile assessment, biologic activity assay, and MHC/HLA. In a preferred embodiment, standard operating procedures (SOPs) and GMP processes are developed to enable manufacturing for most commercial applications.

In another embodiment, the primary human Sertoli cells are cultured in transwell chambers that are coated with extracellular matrix until the cells become confluent and form tight junctions forming polarized monolayers. This system can be used for assessment of toxicity of compounds or mixtures of compound to the Sertoli cells by measuring apoptosis and monitoring the maintenance of the polarized monolayer. In addition, this three-dimensional system can be used to assess the ability of compounds to cross the blood-testis barrier. This has significance for the bioactivity of some types of drugs, for example, anti-HIV and other types of antiinfective agents, and in studying the potential of various compounds for toxicity to the male reproductive system.

There is a great need for more less costly and time-consuming methods of assessing effects on reproductive function and toxicity. A male reproductive toxicology study uses approximately 1120 animals, and the cost is about $200,000. A two-generation study uses approximately 2100 animals at a cost of about $500,000.

There is significant public and scientific concern regarding male reproductive health because of the decrease in the quality of semen, and increase in congenital problems of the urogenital tract and testicular cancers (Hauser 2006). Potential toxicants include phthalates, some pesticides, and polychlorinated biphenyls (PCBs). Less expensive and more mechanistic in vitro screening methods (Brent 2004) could aid in pinpointing environmental chemicals or mixtures of chemicals that are causal for the decline in male reproductive health. The cell-based model of the human BTB proposed herein could cost-effective and highly accurate system for assessing toxicity that acts on Sertoli cells.

In another aspect human Sertoli cells could be useful in cell-based therapy for male infertility that is due to a deficiency of or defects in supporting cells.

Multicellular three-dimensional model systems could be established. For example, Sertoli cells co-cultured with spermatogonia, and the testosterone-secreting Leydig cells could be used to create a model of spermatogenesis (Hadley, Byers et al. 1985; Yu, Sidhu et al. 2005) that would have applications in toxicology, as well as in the development of new types of contraceptive agents, such as those that act on inhibition of cell junctions, and for studies of infertility and normal reproductive biology.

The present invention may be better understood with reference to the following examples. These examples are intended to be representative of specific embodiments of the invention, and are not intended as limiting the scope of the invention.

Examples

Example 1. Isolation of Cells from Cadaveric Tissue and Characterization

Introduction

Cell cultures isolated from donor tissue were high purity Sertoli cells based on the biochemical markers that they expressed, like, follicle stimulating hormone receptor (FSHr) and GATA4, and ultrastructural studies that demonstrated the presence of smooth endoplasmic reticulum and perinucleolar spheres as described below. The data indicated that conditioned medium from these cultures had the ability to inhibit the proliferation of a human lymphocyte cell line, and demonstrate that the proliferative human Sertoli cells maintain their immune-privileged ability in culture. The cultured Sertoli cells proliferated in vitro under normal growth conditions (in the absence of any hormone treatment). The rate of proliferation (doubling approximately every 4 days) was not as robust as transformed cells. In addition, the cells demonstrated growth inhibition from compaction and cell-cell contact, characteristics of primary cells that have the potential to proliferate. We have successfully frozen and propagated the cells without compromising any of the characteristics.

Isolation of Primary Human Sertoli Cells.

Testes were obtained from adult men who had recently undergone brain death. Isolation and culture of human Sertoli cells was performed generally according to a previously described method (Lipshultz, et al., 1982). All solutions, surgical instruments and glassware were sterile. The tissue was transferred to 150 mm tissue culture dish and washed with ice cold Hank's Balanced Salt Solution (HBSS) containing 100 U/ml penicillin and 100 µg/ml streptomycin. The dense collagenous connective tissue, the tunics albuginea, was removed using a scissors and the tissue was transferred to ti fresh petri dish and rinsed several times with HBSS and minced into tiny pieces. The minced tissue was transferred to 1,000-ml Erlaenmeyer flask; washed three times with HBSS discarding the media after each wash, and then covered with HBSS and transferred to a 37° C. water bath and shaken at 325 rpm for 15 min. The tissue was allowed to settle, the supernatant was discarded, and 50-ml of HBSS containing 0.25% trypsin (Sigma, St. Louis, Mo.), 0.1% collagenase Type IV (Sigma) and 2.4 µU dispase/ml (Roche, Indianapolis, Ind.) was added. The flask was shaken at 325 rpm at 37° C. for 20 min. Then the solution was strained through a coarse wire mesh, the flow-through stored on ice, and the undigested tissue pieces were again placed in HBSS containing the same enzyme mixture, and shaken at 325 rpm at 37° C. for 15 min. These steps were repeated until most of the tissue was digested. Finally, 0.034% of soybean trypsin inhibitor (Sigma) was added. The solution was passed through a syringe with an 18-gauge needle, and then centrifuged at 800×g for 5 min. The supernatant was discarded and the cell pellet resuspended in tissue culture medium (Dulbeccos Modified Eagle medium (DMEM):F-12 Hams medium, 50:50, containing 100 U/ml penicillin and 100 µg/ml streptomycin, 5% fetal bovine serum) and plated in a T-225 flask. Cell viability was determined by exclusion of trypan blue dye.

The cells were propagated in the same medium containing 5% fetal bovine serum, and incubated at 37° C. in a 5% $CO_2$ incubator. The cells reached confluence 3-5 weeks after first observing cells adhering to the flask at which point they were passaged. Some of the cells were frozen in cell preservation medium and stored under liquid nitrogen.

Light microscopy was performed using an inverted Olympus microscope and observation of the culture flask containing the cell pellet revealed only cell debris and many dead cells over the first few days toweeks. No cells adhering to the surface of the flask were observed. At 2-20 days post-isolation, a few thin, long cells were observed adhering to the bottom of the culture flasks. At first all that could be seen were a few groups that each contained only a few (2-10) cells. But within a few days of the first observation, the cells began to flatten out and their bodies became polygonal with extensive branching cytoplasmic structures that are characteristics indicative of Sertoli cells (FIGS. 1A-1D) (Lipshultz; Murthy et al. 1982; Teng, Xue et al. 2005). The groups of cells also began to multiply locally, but in addition a few cells or groups of cells were observed at locations well-separated (5-10 cm) from any other cells.

The first observation of adherent cells was at approximately 3 weeks after the isolation procedure was performed in each of the two successful protocols. In subsequent isolations adherent cells were observed sooner, in approximately 3-7 days. Only two to three isolated groups of only 3-4 cells each were observed at first. The cells expanded out from each of these locations, and one or a few cells were observed at locations entirely separated from other cells over time. The cells at each location appeared to grow n a local fashion. The cells reached confluence in the original flask after approximately 6-7 weeks and then the cells were trypsinized, and either passaged or frozen in cell preservation medium in liquid nitrogen.

Characteristic features of Sertoli cells include a large irregularly-shaped nucleus, extensive and branching cytoplasmic structures, prominent nucleoli, perinucleolar spheres, lipid droplets, and abundant smooth and rough endoplasmic-reticulum. The oval to pyramidal shape of the nucleus and the extensive and branching cytoplasmic structure of the cells can be observed in bright-field photomicrographs (see FIGS. 1A-1D).

Cultures from 5 donors have been established: MM-HSE-2305; MM-HSE-2905; MM-HSE-2106; MM-HSE-1906; and MM-HSE-2306. Frozen cultures haven been thawed and then passed in culture after more than 1 year in liquid nitrogen storage. Early passage cultures (<4) have been expanded and vials of frozen stock put in storage. Some cultures have been continuously maintained by passage for more than 6 months, and have been passaged more than 8 times. For staining purposes, cells from both cultures were plated in 8-well chamber slides. Conditioned medium for the lymphocyte proliferation assay was harvested after 48-hours from cell cultures that were 70-80% confluent.

Sertoli cells are thought to represent a fixed population of non-dividing support cells once a human male is past puberty. Previous reports of the isolation of primary human Sertoli cells described finding them attached to the culture flasks within 2-3 hours of plating and forming a confluent monolayer in the culture dish within 24-48 hours (Lipshultz, Murthy et al. 1982; Teng, Xue et al. 2005).

The methods that we used in isolation of the proliferative human Sertoli cells differed from those employed in other laboratories (Lejeune, Sanchez et al. 1998; Teng, Xue et al. 2005), and was adapted from techniques used by Lipshultz et al. (Lipshultz, Murthy et al. 1982). who incubated testes tissue in a shaking water bath at a much higher speed (1,500 oscillations per minute) at 37° C. Lejeune et al. Isolated fragments of seminiferous tubules by filtering testes tissue after collagenase and deoxyribonuclease digestion for 90-120 min and then isolating tubule fragments by gravity sedimentation, and performing a second digestion with trypsin and additional gravity sedimentations (Lejeune, Sanchez et al. 1998). Teng et al. used trypsin to digest testes tissue before digestion with hyaluronidase and collagenase Type 1 (Tang, Xue et al. 2005). The protocol that we used also differed from those employed for rat Sertoli cells that are typically isolated from the testes of pups of 15-20 days of age (Karl and Griswold 1990; Korbutt, Elliott et al. 1997; Trivedi, Igarashi et al. 2006).

In our work with primary rat Sertoli cells (Trivedi, Igarashi St al. 2006), we found that the freshly isolated cells could be frozen and then placed again in cell culture successfully. However, rat Sertoli cells did not proliferate significantly and were viable in culture for only approximately 6 weeks. In vivo the proliferation of rat Sertoli cells increases from day 16 to day 20 of gestation that is two days before birth, and then decreases until ceasing by 21 days after birth (Orth 1982).

Figure 2:
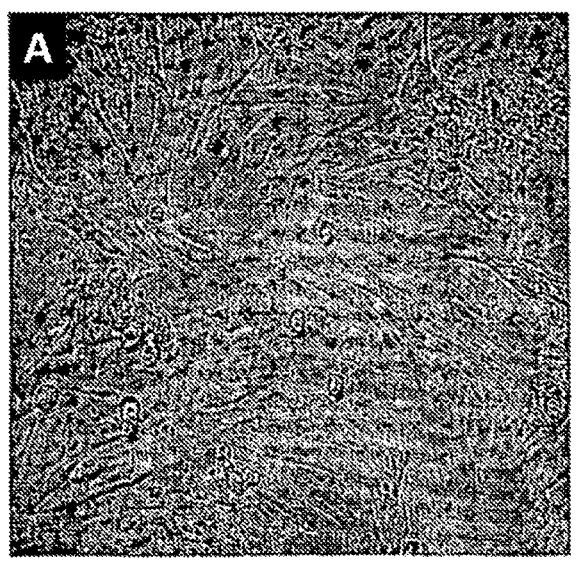
FIG. 2A is a bright-field photomicrograph of Sertoli cells isolated from rat neonates.
FIG. 2B is a bright-field photomicrograph of human Sertoli cells isolated from adult cadaveric donor tissue after approximately 3 weeks in identical culture conditions.
Figure 2:
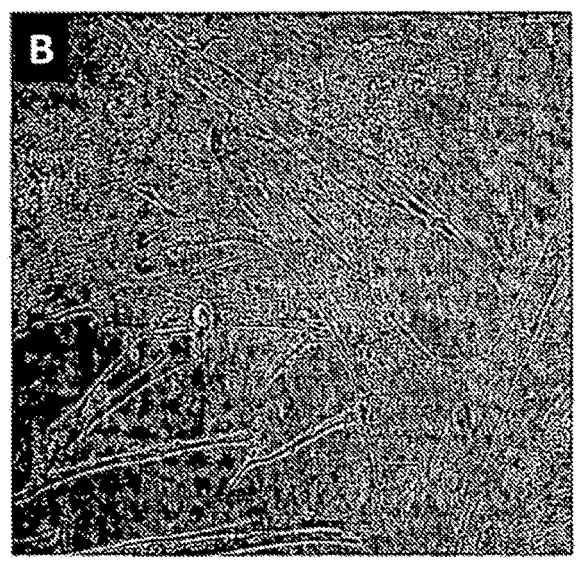

A bright-field photomicrograph of rat Sertoli cells isolated from neonates and human Sertoli cells isolated from adult cadaveric tissue after approximately 3 weeks in identical culture conditions (see FIGS. 2A and 2B) illustrate the more clearly defined cell processes and healthier appearance of the human compared to the rat cultures. The slight differences that could be observed at 3 weeks became more pronounced over time—until 6-8 weeks when few of the rat Sertoli cells were alive whereas the humancells maintained their healthy appearance.

Immunocytochemical Characterization

To determine the purity of the Sertoli cell cultures, cells were immunostained with the Sertoli-cell specific marker, follicle stimulating hormone receptor (FSHr), using a sheep anti-FSHr antibody (Biogenesis, Poole, UK), or with GATA-4 (Santa Cruz Biotechnology, Santa Cruz, Calif.). At 60-70% confluence, Sertoli cells were fixed in 4% paraformaldehyde (PFA) for 30 min, and then rinsed three times in phosphate buffered saline (PBS) for 5 minutes. For FSHr staining, slides were incubated in each of the following solutions sequentially: 2% rabbit serum/0.2% Triton X-100/ 0.1% bovine serum albumin (2% RS/TX/BSA) for 10 minutes; 10% RS/TX/BSA for 20 minutes; polyclonal antibody directed against FSHr to label Sertoli cells (4 g/ml in 2% RS/TX/BSA) overnight; rinsed in PBS; biotinylated rabbit anti-sheep IgG (1:150 in 2% RS/TX/BSA; Vector Laboratories, Burlingame, Calif.) for 1 hour; and rinsed again in PBS. Immunoreactivity was visualized by fluorescence microscopy using avidin-conjugated Texas red (1:200 in PBS; Vector Laboratories). In addition, cell nuclei were stained with 1x bisbenzamide for 2 min, washed with PBS, and mounted using Aqua mount (Biomeda, Foster City, Calif.) then kept at 4° C. until analyzed.

For GATA-4 immunolabeling, slides were blocked with 2% goat serum/0.2% Triton X-10010.1% bovine serum albumin (2% GS/TX/BSA) for 10 minutes; 10% GS/TX/BSA for 20 minutes; incubated with polyclonal antibody directed against GATA-4 (1:50 in 2% GS/TX/BSA; Santa Cruz Biotechnology) overnight; rinsed in PBS, and incubated in biotinylated goat anti-rabbit antibody (1:200, Vector Laboratories) for 1 hour; and rinsed again in PBS. Immunoreactivity was visualized by fluorescence microscopy using the avidin-conjugated FITC (1:200, Vector Laboratories) with incubation for 1 hour, washing and mounting with Aqua mount (Biomeda, Foster City, Calif.) and storage at 4° C. until analysis.

Figure 3:
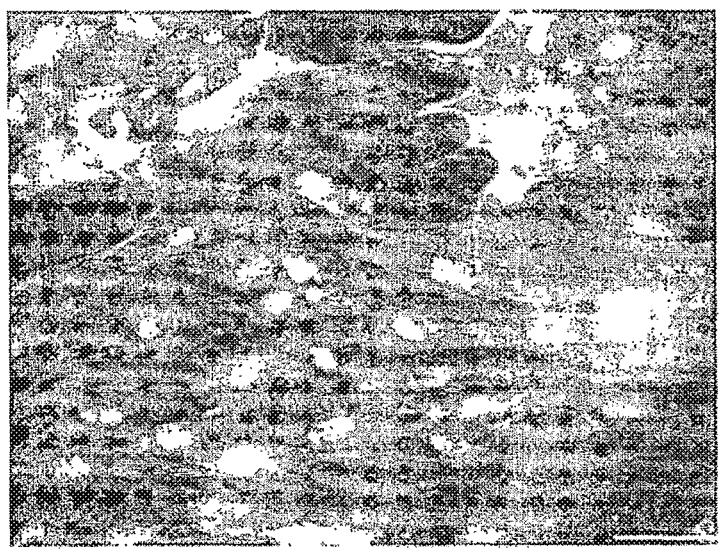
FIG. 3 is a fluorescence photomicrograph of MM-HSE-2305 cells immunostained for GATA-4 that is expressed in the testes only in Sertoli and Leydig cells after puberty (20×; scale bar 50 µm).

The MM-HSE-2305 cells were immunochemically stained for molecules that are specifically expressed by Sertoli cells. In FIG. 3 is presented a photomicrograph of MM-HSE-2305 cells labeled with an antibody to GATA-4

(green). GATA-4 is a zinc-finger transcription factor that is expressed in Sertoli cells in human testes and that is critical in the regulation genes involved in Sertoli cell differentiation, the regression of the Mullerian duct, and the initiation of testosterone production (Ketola, Pentikainen et al. 2000; LaVoie 2003).

Figure 4:
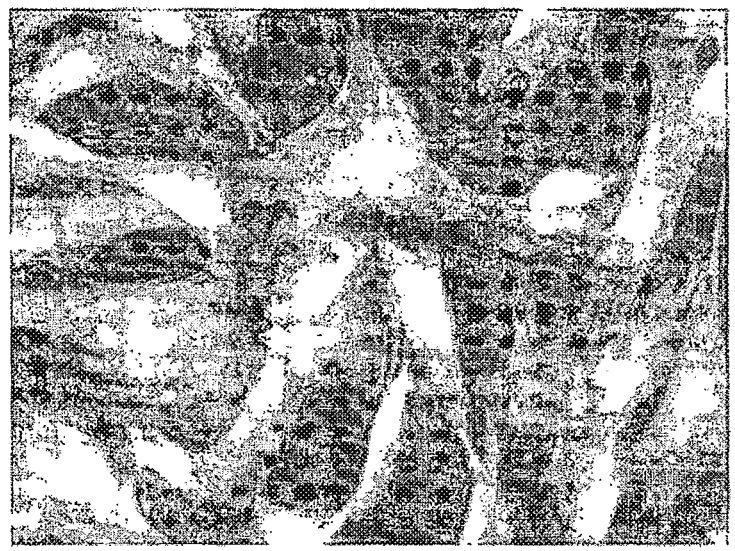
FIG. 4 is a fluorescence photomicrograph of MM-HSE-2305 cells immunostained for the follicle-stimulating hormone receptor (FSHr) that is expressed only by the Sertoli cells in the testes (50×). The nuclei of the cells were stained with bisbenzamide (Hoescht) dye (blue).

A photomicrograph is presented in FIG. 4 of MM-HSE-2305 cells stained with antibody to FSHr (red) along with bisbenzamide counterstaining to reveal each individual nucleus. Receptors for FSH are solely localized on the Sertoli cells in the testis and on the granulosa cells in the ovary (O'Shaughnessy, Dudley et al. 1996). Purity was determined by the counting number of cells stained by FSHr divided by the number of nuclei stained by bisbenzamide. Nuclei stained with bisbenzamide represented the total number of cells.

A small number of human Leydig cells were isolated in the preparations. The identity of these cells could be distinguished as Leydig due to their demonstration of a distinctive cobblestone type appearance differing from the Sertoli cells. These data definitively establish the identity of the Sertoli cells and the purity of the cultures was estimated at more than 95% based on the immunocytochemical analyses as described in the methods section.

Proliferation of Human Sertoli Cells.

Figure 5:
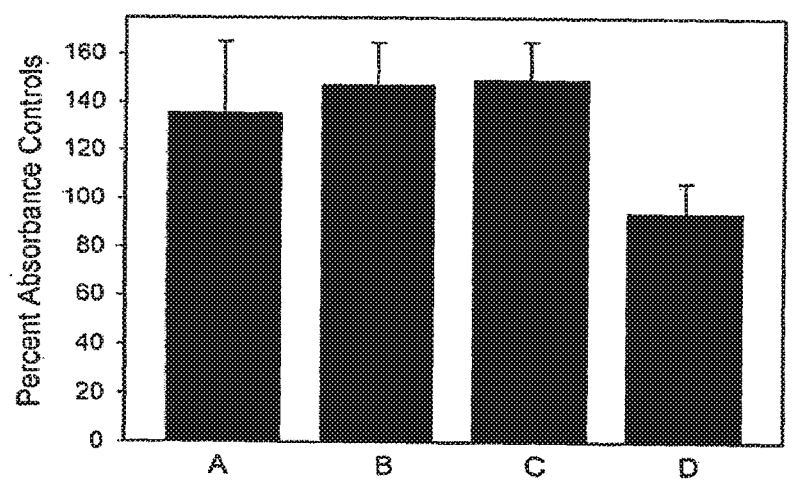
FIG. 5 is a graph representing the proliferation of MM-HSE-2305 cells (passage 5) in 48 h is shown. The absorbance of WST-1 at 72-h is presented as a percentage of that at 24 h. The cells were plated at varying concentrations ranging from $0.5 \times 10^3$ (A), $1.0 \times 10^3$ (B), $2.0 \times 10^3$ (C), to $4.0 \times 10^3$ (D) cells per well (1,500 to 12,000 per cm$^2$). The number of cells in the wells that were plated at $1.0 \times 10^3$ (B) and $2.0 \times 10^3$ (C) cells per well increased by almost 50% (P=0.0.006, P=0.004, respectively) in 48-h. Similar results were obtained in three separate experiments. The data presented are the means with ±SD from two separate experiments with each concentration of cells tested in quadruplicate.

To quantify their proliferation, $0.5 \times 10^3$, $1.0 \times 10^3$, $2.0 \times 10^3$, or $4.0 \times 10^3$ MM-HSE-2305 cells (passage 5), were plated in 96-well tissue culture plates. The 96-well plates were incubated at 37° C. in a 5% $CO_2$ incubator. The relative number of cells per well was determined from absorbance due to the active metabolism of the cell proliferation reagent WST-1 (Roche). At 24 h post plating the above mentioned numbers of cells, WST-1 was added and total cell numbers were quantified in quadruplicate wells and defined as 100%. At 72 h post plating, quadruplicate wells were analyzed with WST-1 as above. Proliferation over a 48 h-period was assessed by comparing the WST-1 absorbance of wells analyzed at 24 h to that of wells analyzed at 72 h post-plating. The WST-1 absorbance was measured at 450-nm on a Thermomax microplate reader (Molecular Devices, Sunnyvale, Calif.). WST-1 (10 µL) was added to the wells and the absorbance of WST-1 was measured 2 h after it was added. Background from the slight spontaneous absorption of medium alone with WST-1 was subtracted from the reading for each well. Values represent the mean±SD and experiments were performed in triplicate. After 48 h there were more cells in the wells that were plated with $1.0 \times 10^3$ (P=0.006) or with $2.0 \times 10^3$ (P=0.004) cells per well compared to control wells with a mean increase of 48% as shown in FIG. 5. However, the number of viable cells did not increase in the wells that were plated with a higher number, $4.0 \times 10^3$ cells, per well. All mean and standard deviation were calculated from individual values in each group.

The proliferation rate of the MM-HSE-2305 cells from passage 5 when fewer cells ($0.5 \times 10^3$, $1.0 \times 10^3$, or $2.0 \times 10^3$) were plated per well corresponded to a doubling time of approximately every 4 days according to the WST-1 assay. However, as shown in FIG. 5 when the cells were plated close to confluence at $4.0 \times 10^3$ cells per well there was little proliferation in 48 h. These data illustrate the proliferation of the human Sertoli cells and demonstrate the growth inhibition from compaction and tight cell-cell contact that was observed and that is a characteristic of normal cells (Huang and Ingber 1999).

The results obtained with the MM-HSE-2305 cells (passage 5) in the proliferation assay were consistent with analyses of the doubling time of the other primary human Sertoli cell cultures. This result also is consistent with the length of time required for the cells from the initial isolation to proliferate until becoming confluent. If there were 80 viable proliferative human Sertoli cells isolated originally, for example with a 3-day average doubling time, the population would reach $2 \times 10^6$ (2 million) in approximately 6% weeks. This is in accordance with what was observed. In general, the proliferation of the cells decreased somewhat with more doublings and passages, in addition to slowing down as the cells became closer to confluence.

With our method as described above very few Sertoli cells were detected adhering to the culture dish originally. Thus, the viable Sertoli cells that were isolated must have represented only a very small percentage of the Sertoli cells in the testes that in adult men number approximately 4 billion (Johnson, Zane et al. 1984; Cortes, Muller et al. 1987). Despite the isolation of only a few Sertoli cells, these proliferated in the original flask until becoming 70-80% confluent. Initially subcultures were formed with split ratios of 1:5 to 1:10. Subsequent studies showed that if the split ratio was decreased several fold, the cells continued to proliferate. Thus, the population of cells from the original flask (~3-4×10⁶ cells in a T-225 flask) theoretically can be expanded by simply plating them at low densities such that from a single donor it is possible to obtain more than the maximal number of Sertoli cells that could be obtained from testes from 10-20 individual donors within a few passages.

Proliferation of Human Sertoli Cells in Response to FSH Treatment

It has been reported that cultured rat Sertoli cells, proliferate in response to recombinant FSH (Buzzard, Wreford et al. 2002). We determined the response of the human cells to FSH treatment to provide further evidence that they are Sertoli cells. The human Sertoli cells (MM-HSe-2305 cells; 7,000 per well) were placed in 8-well chamber slides and incubated with control media or with media containing 200-ng/ml FSH (Sigma-Aldrich) for 1 week. Then the cells were labeled with BrdU that is incorporated into nuclei during DNA synthesis prior to mitosis. The slides were stained with anti-BrdU antibody (finally stained by Texas red) followed by staining with an antibody to FSHr (finally with FITC), and nuclei marked by bisbenzamide.

Briefly, the MM-HSE-2305 cells were labeled with BrdU (Roche; 100 µM) at 37° C./15% $CO_2$ for 2 hours then washed three times with PBS followed by fixing with 4% PFA for 30 min. After washing, the 8-well slide was blocked with 10% GS/TX/BSA for 20 min, with 2% GS/TX/BSA for 10 min then incubated with monoclonal anti BrdU (1:1000, Sigma) overnight. On the next day, the slide was washed with PBS three times before incubating with biotinylated goat anti-mouse (1:200, Vector Laboratories) for 1 hour at room temperature. Fluorescence was enhanced by incubating with ABC solution (Vector laboratories) for 30 min. Immunoreactivity was visualized by fluorescence microscopy using avidin-conjugated Texas red (1:200 in PBS) for 1 hour.

Photomicrographs were taken with different filters of the same field. The percentage of proliferating Sertoli cells was determined by the counting the number of FSHr, BrdU double positive cells and dividing this by the total number of cells per field.

Figure 6:
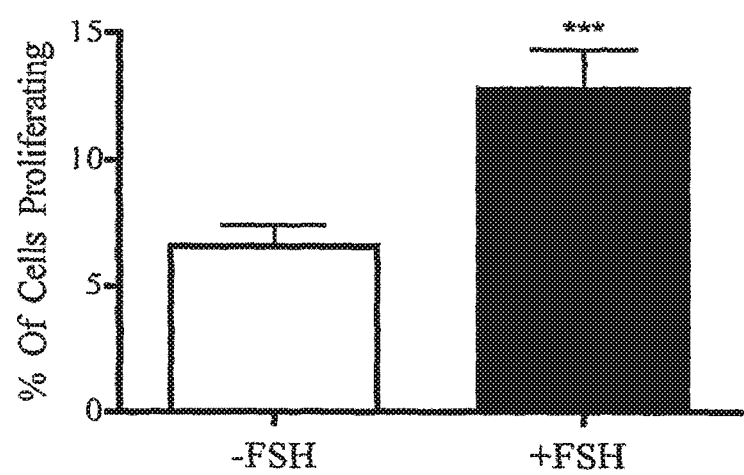
FIG. 6 is a graph representing the proliferation of MM-HSE-2305 cells in the presence and absence of 200 ng/ml FSH.

The results are presented (see FIG. 6) graphically from analysis of >50 fields. These revealed that without FSH treatment 6.58 percent of the cells were undergoing proliferation as shown. Between groups, a Student's t-test was used to compare the data (SigmaStat, Version 3.01). The percent of cells undergoing proliferation increased significantly with FSH treatment to 12.35 (p<0.001). The increased proliferation of the cells in response to FSH treatment is further evidence that the isolated cells are human Sertoli cells.

Proliferation of T Lymphocytes in Human Sertoli Cell Conditioned Media

Conditioned media were collected after 48-hr incubation with cultures (70-80% confluent) of MM-HSE-2305, MM-HSE-2905 and MM-HSE-2106 and of a human foreskin fibroblast cell line HS-27, obtained from the American Type Culture Collection (ATCC, Manassas, Va.). The conditioned medium from the HS-27 cell line served as a negative control for the assay. The experiment was performed in a 96-well tissue culture plate and each concentration of conditioned medium was tested in triplicate. The experiments were each repeated three or more times. Each well had a total volume of 120 µL, with $1.5 \times 10^4$ human lymphocytes (human T cell line, Jurkat E6, obtained from ATCC, maintained in RPMI 1640 media with 20% FBS, 1× penicillin-streptomycin) placed in the presence of either varying amounts of Sertoli or HS-27 fibroblast cell conditioned media or with unconditioned media containing FBS and 1× penicillin-streptomycin, (DMEM:F-12 Hams medium, 50:50, containing 0.5% FBS for Sertoli and DMEM with 10% FBS for fibroblasts) serving as media controls. The 96-well plate containing different concentrations of conditioned medium or control medium was incubated at 37° C. in a 5% $CO_2$ incubator for 72 hours. Then the relative proliferation of the lymphocytes in each well was determined by active metabolism of WST-1. After 2-4 hours incubation with 12 µL of WST-1, the absorbance was measured at 450-nm by a Thermomax microplate reader with the absorption of the medium alone with WST-1 subtracted from the reading for each well.

Figure 7:
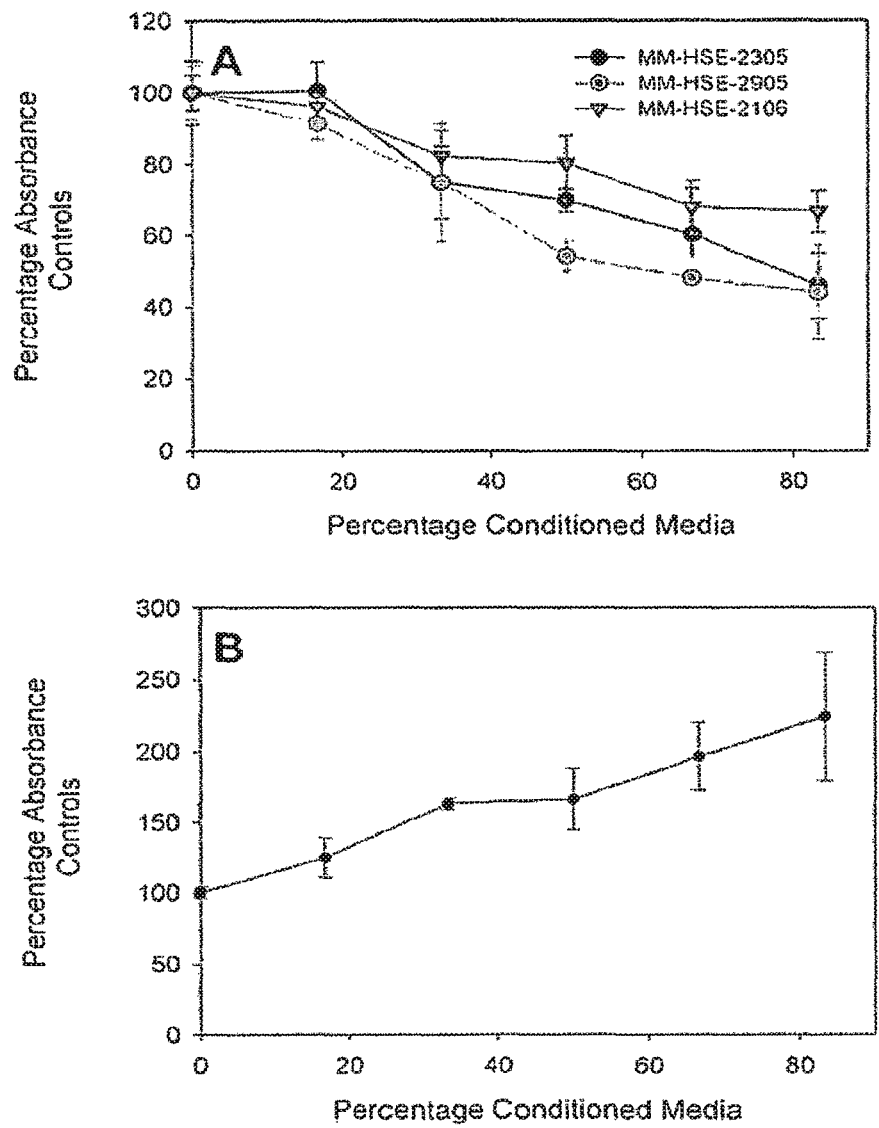
FIG. 7A presents graphs of the increasing concentration of conditioned media from the MM-HSE-2305, MM-HSE2905, and MM-HSE-2106 cells versus the number of viable T-lymphocyte cells per well.
FIG. 7B presents graphs of the increasing concentration of conditioned media from the human foreskin fibroblast cell line, HS-27, versus the number of viable T-lymphocyte cells. The number of viable cells is presented as a percentage of control well absorbance as revealed by active metabolism of WST. With the HS-27 media in FIG. 7B, there was a significant increase in the number of viable cells in the wells treated with conditioned media compared to control wells at each point (p<0.05). The proliferation of lymphocytes in FIG. 7A was significantly decreased by conditioned media from each of the 3 human Sertoli cell cultures (two way ANOVA, p<0.001 for media from each culture). Data are presented as the mean with ±SD from two separate experiments with each concentration tested in triplicate.
Figure 8:
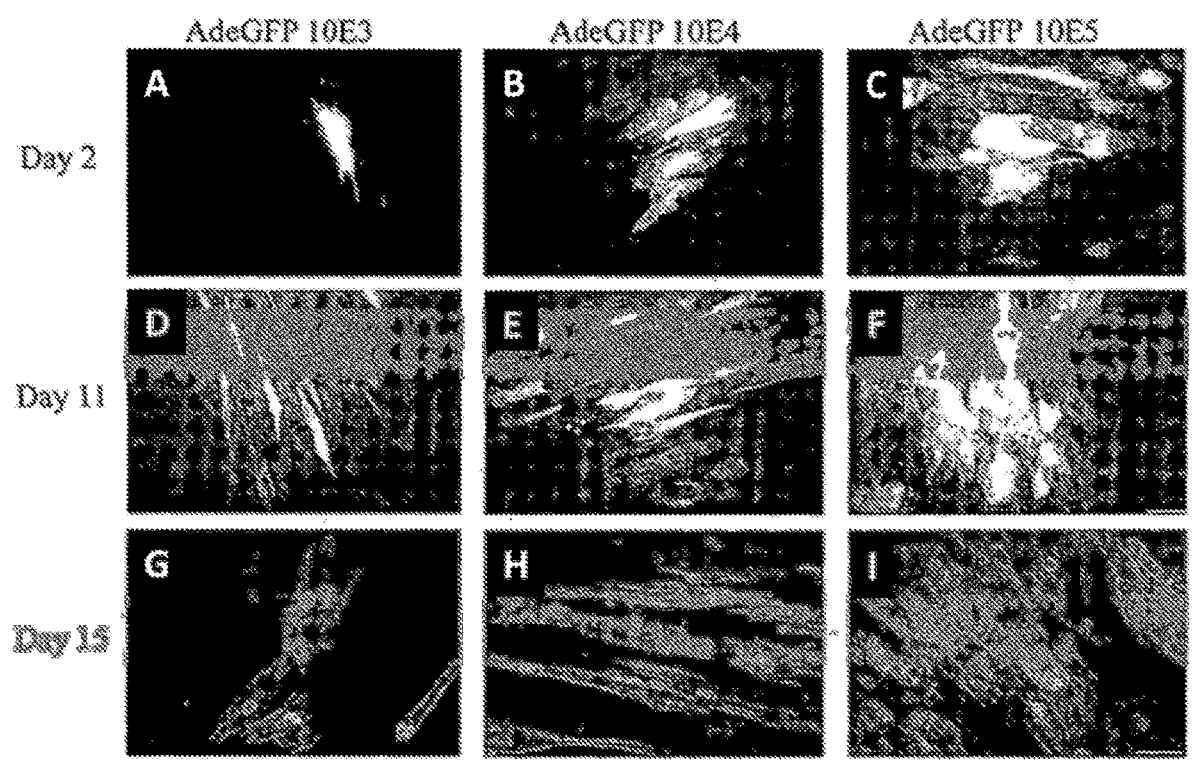
FIG. 8A is a fluorescence photomicrograph of MM-HSE-2305 cells in culture that have been transformed with $10^3$ viral particles per cell of recombinant adenovirus expressing enhanced green fluorescent protein (eGFP) at day 2 post infection.
FIG. 8B is a fluorescence photomicrograph of MM-HSE-2305 cells in culture that have been transformed with $10^4$ viral particles per cell of recombinant adenovirus expressing enhanced green fluorescent protein (eGFP) at day 2 post infection.
FIG. 8C is a fluorescence photomicrograph of MM-HSE-2305 cells in culture that have been transformed with $10^5$ viral particles per cell of recombinant adenovirus expressing enhanced green fluorescent protein (eGFP) at day 2 post infection.
FIG. 8D is a fluorescence photomicrograph of MM-HSE-2305 cells in culture that have been transformed with $10^3$ viral particles per cell of recombinant adenovirus expressing enhanced green fluorescent protein (eGFP) at day 11 post infection.
FIG. 8E is a fluorescence photomicrograph of MM-HSE-2305 cells in culture that have been transformed with $10^4$ viral particles per cell of recombinant adenovirus expressing enhanced green fluorescent protein (eGFP) at day 11 post infection.
FIG. 8F is a fluorescence photomicrograph of MM-HSE-2305 cells in culture that have been transformed with $10^5$ viral particles per cell of recombinant adenovirus expressing enhanced green fluorescent protein (eGFP) at day 11 post infection.
FIG. 8G is a fluorescence photomicrograph of MM-HSE-2305 cells in culture that have been transformed with $10^3$ viral particles per cell of recombinant adenovirus expressing enhanced green fluorescent protein (eGFP) at day 15 post infection.
FIG. 8H is a fluorescence photomicrograph of MM-HSE-2305 cells in culture that have been transformed with $10^4$ viral particles per cell of recombinant adenovirus expressing enhanced green fluorescent protein (eGFP) at day 15 post infection.
FIG. 8I is a fluorescence photomicrograph of MM-HSE-2305 cells in culture that have been transformed with $10^5$ viral particles per cell of recombinant adenovirus expressing enhanced green fluorescent protein (eGFP) at day 15 post infection.

Data are presented as the mean with ±SD from two separate experiments with each concentration tested in triplicate (see FIGS. 7A and 7B). With the HS-27 media (see FIG. 7B), there was a significant increase in the number of viable cells in the wells treated with conditioned media compared to control wells at each point (p<0.05). The proliferation of lymphocytes was significantly decreased (see FIG. 7A) by conditioned media from each of the 3 human Sertoli cell cultures (two way ANOVA, p<0.001 for media from each culture). For this assay the data was analyzed by two way ANOVA followed by Bonferroni's post hoc analysis (Graphpad Prism, Version 4.03).

The data indicate that the MM-HSE-2305, MM-HSE-2905, and MM-HSE-2106 cells secrete molecules into the culture media that inhibit the proliferation of the T lymphocytes. Conversely, HS-27, the cultured human fibroblast cell line, secreted molecules that stimulated lymphocyte proliferation in vitro, in accordance with the common use of conditioned media from fibroblasts to stimulate proliferation of various cultured cells.

The immunosuppressive activity of the Sertoli cell condition medium is likely to be diagnostic of the activity of Sertoli cells that is thought to be required for maintenance of the blood-testis barrier (Wyatt, Law et al. 1988; Turek, Malkowicz et al. 1996; Li, Ren et al. 1997; Braendstrup, Bols et al. 1999; Suarez-Pinzon, Korbutt et al. 2000) in addition to physical isolation (Pelletler and Byers 1992). The Fas/Fas ligand system that functions in immmunomodulation has been reported to be expressed by human testicular tissues in several (Sugihara, Saiki et al. 1997; Xerri, Devilard et al. 1997; Braendstrup, Bols at al. 1999: Francavilla, D'Abrizio et al. 2000) but not all studies (Kimmel, Ohbatake et al. 2000), and there is evidence in mice that expression of Fas ligand by Sertoli cells is critical for prevention of allograft rejection (Bellgrau, Gold et al. 1995). The expression of both transforming growth factor (TGF)-beta and Fees ligand were important in induction of systemic tolerance to antigen by its injection into the testes (orchidic tolerance) of rats (Li, Ren et al. 1997). In addition, TGF-beta was found to be essential for the prevention of the autoimmune destruction of beta islet cells by Sertoli cells co-implanted in NOD mice (Suarez-Pinzon, Korbutt et al. 2000).

Due to their immunosuppressive ability the proliferative human Sertoli cells could be well-suited for allogeneic transplantation for cell therapy, and for co-transplantation to protect co-implanted cells from rejection stimulated to alloreactivity or autoimmune reactions.

Example 2. Genetic Modification of Proliferative Primary Human Sertoli Cells

To determine if the cells could be genetically modified to express a protein of Interest for use in cell based gene delivery protocols, they were modified to express a reporter molecule, the green fluorescent protein (GFP). Cells were plated in 8-well tissue culture slides at approximately 20,000 cells/well. When about 80-90 percent confluent, the cells were infected with adenovirus vector expressing eGFP under cytomegalovirus promoter (Ad5eGFP). Adenovirus vector was obtained from ViraQuest (North Liberty, Iowa). There were two wells per condition that were (a) no virus, (b) 10 viral particles/cell, (c) $10^4$ viral particles/cell (d) and $10^5$ viral particles/cell. Cells were infected in the absence of serum and virus was left in for 4 hours. At the end of the incubation, virus containing medium was removed and fresh medium containing serum was added to the cells. This inhibits any further infection of the cells. Cells were checked at day one and weekly thereafter. Medium was changed every two to three days. Cells in culture were imaged on an inverted fluorescent microscope attached to an Olympus camera using a FITC filter. At the end of the experiment, cells were fixed in 4% PFA and imaged on Nikon microscope attached to SPOT Camera using FITC filter.

The fluorescence photomicrographs (see FIGS. 8A-8I) of human Sertoli cells in culture taken 2, 11, and 15 days after infection with $10^3$, $10^4$, $10^5$ Ad5eGFP particles per cell show that cells infected with the lower number of viral particles per cell appear healthier with better definition of the cellular processes.

Figure 9:
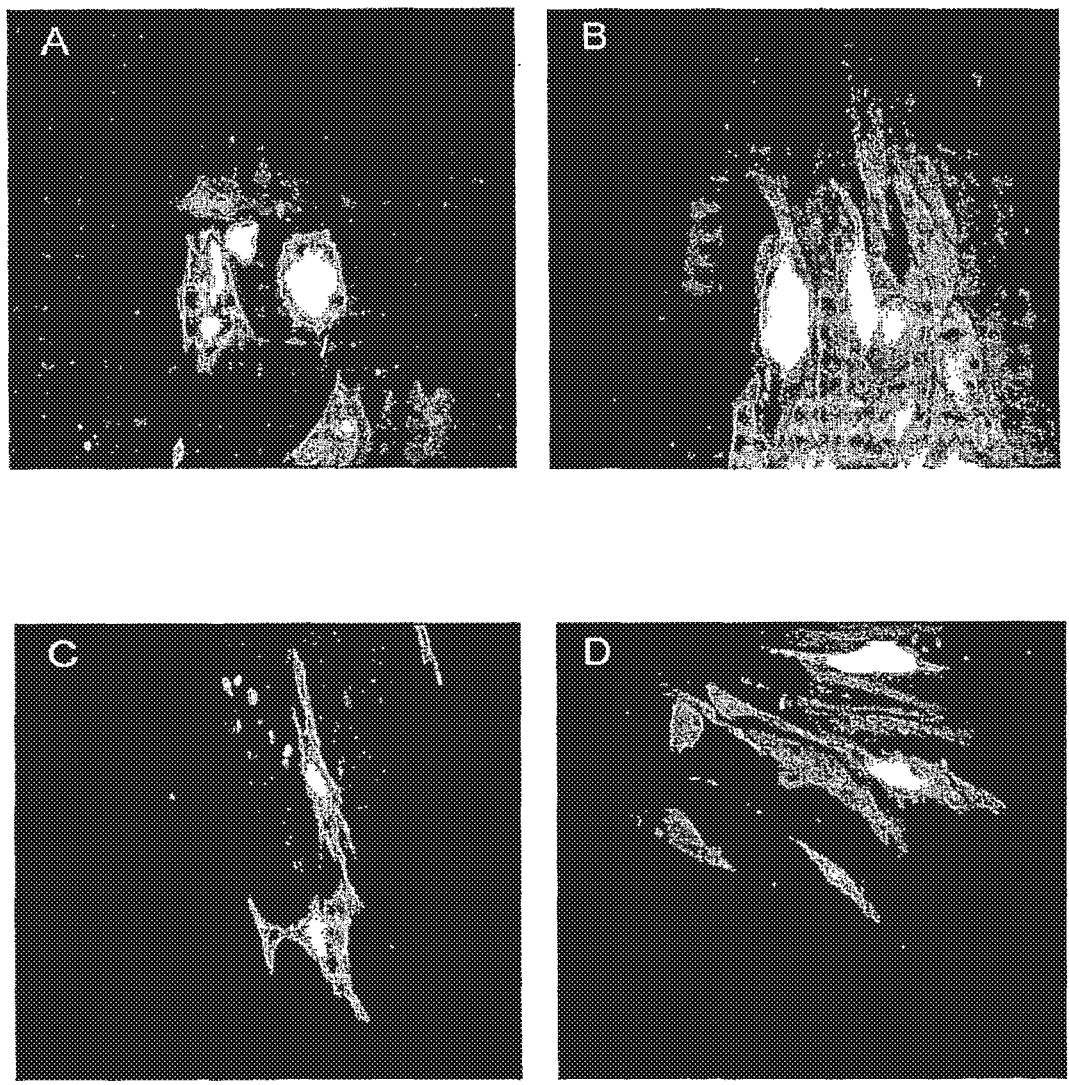
FIG. 9A is a fluorescence photomicrograph of rat Sertoli cells taken 21 days after infection with $1 \times 10^4$ particles of Ad5eGFP per cell.
FIG. 9B is a fluorescence photomicrograph of human Sertoli cells taken 21 days after infection with $1 \times 10^4$ particles of Ad5eGFP per cell.
FIG. 9C is a fluorescence photomicrograph of rat Sertoli cells taken 35 days after infection with $1 \times 10^4$ particles of Ad5eGFP per cell.
FIG. 9D is a fluorescence photomicrograph of human Sertoli cells taken 35 days after infection with $1 \times 10^4$ particles of Ad5eGFP per cell. Cells in FIG. 9A and FIG. 9B were plated on the same day. Cells in FIG. 9C and FIG. 9D were plated on the same day.

The viability and efficiency of modification of the human Sertoli cells was compared to that of rat Lewis Sertoli cells isolated as we have previously described (Trivedi, Igarashi et al. 2006) and cultured in Ham's F12 media with 5% FBS and penicillin-streptomycin lx, and with the HS-27 human foreskin fibroblasts cultured as described. Fewer of the modified rat cells (see FIGS. 9A and 9C) could be observed after in vitro culture. There were more of the modified human cells (see FIGS. 9B and 9D) observed at both 21 and 35 days, and the human cells appeared to be in better condition with more distinct morphology and cellular processes. Similar results were obtained in 3 separate experiments testing the ability of the rat Sertoli cells to survive after genetic modification compared to the survival of the human Sertoli cells. The results indicated that the human Sertoli cells were much more viable after genetic modification than the rat Sertoli cells after 21 and 35 days in culture.

Figure 10:
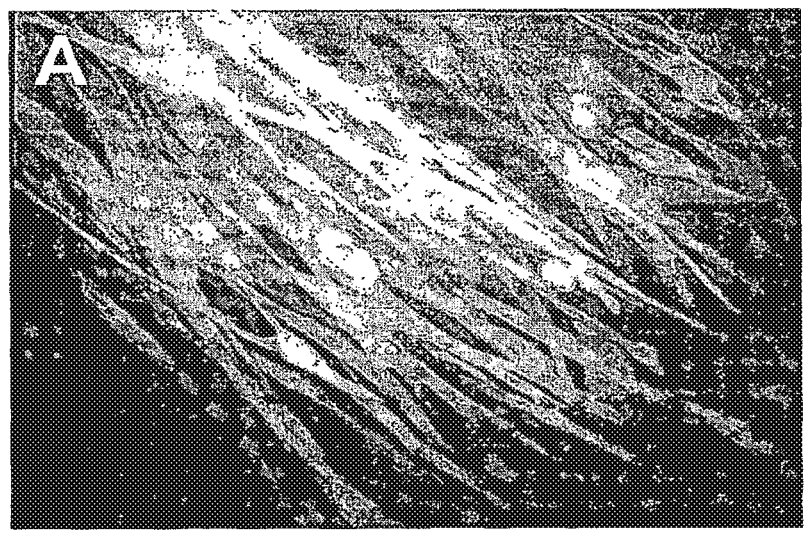
FIG. 10A is a fluorescence photomicrograph of MM-HSE-2305 cells in culture that have been transformed with $10^3$ Ad5eGFP particles per cell of recombinant adenovirus expressing eGFP at 46 days post-infection.
FIG. 10B is a fluorescence photomicrograph of MM-HSE-2305 cells in culture that have been transformed with $10^4$ Ad5eGFP particles per cell of recombinant adenovirus expressing eGFP at 46 days post-infection. The expression of the eGFP by the cells is evident at this time point that is more than 6 weeks after infection.
Figure 10:
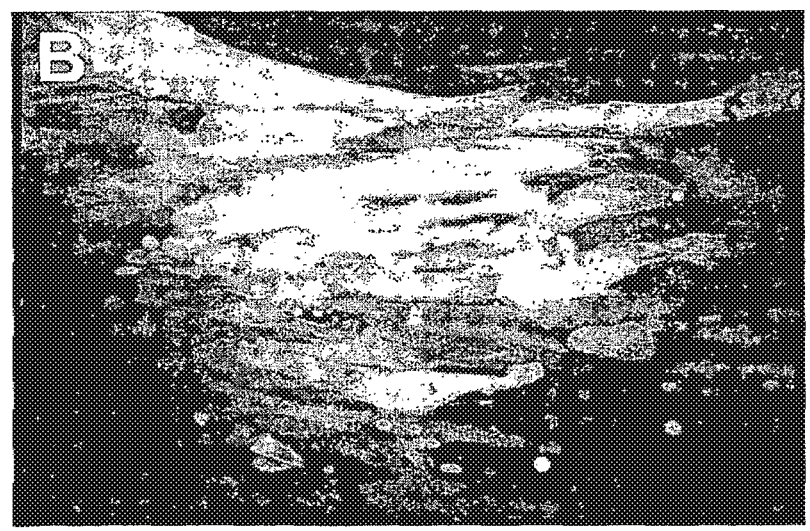

Photomicrographs (see FIGS. 10A and 10B) of human Sertoli cells taken 46 days after infection with $10^3$ (FIG. 10A) and $10^4$ (FIG. 10B bottom) Ad5eGFP particles per cell also indicate that the lower concentration of virus produced genetically modified cells that were healthier for longer time periods. Similar results were obtained in 3 separate experiments with genetically-modified human Sertoli cells. The cells retain the property of growth inhibition from contact and compaction that is a hallmark of differentiated primary cells and thus they should form fewer tumors than transformed cells. Overall, these data indicate that the proliferative primary human Sertoli cells could be well-suited for ex vivo gene therapy applications, for example, for spinal cord injury, such as we have previously described using rat Sertoli cells modified to express recombinant neurotrophin-3 in a rat model spinal cord injury (Trivedi, Igarashi et al. 2006).

Example 3. Model of Human Blood-Testis Barrier

The specialized tight junctions (TJs) that occur in the testes between Sertoli cells create the polarity of the cells, restrict the movement of molecules between them, and separate the seminiferous epithelium into basal and adluminal compartments. Studies with rodent Sertoli cells have shown that formation of polarized monolayers can be achieved by growing the cells on or in extracellular matrix (ECM) on permeable supports such as transwell chambers (Hadley, Byers et al. 1985; Janecki and Steinberger 1986; Hadley, Djaklew et al. 1987; Anthony and Skinner 1989; Onoda, Suarez-Quian et al. 1990; Steinberger and Klinefelter 1993). Some of these monolayers were shown to have basally located tight junctions and to maintain germ cells (Yu, Sidhu et al. 2005). The formation of the barrier is assessed by its ability to stop the flow of media, the increase in transepithelial electrical resistance (TER), and polarized secretion of transferrin. This type of system can be used as a model of the blood-testis barrier (BTB) by assessing the ability of compounds to cross through the monolayer, their effect on the barrier itself, and on the viability of, or the induction of cell death in the Sertoli cells. In the past these model systems have been established with Sertoli cells from other species such as rat due to the difficulties in obtaining adequate numbers of human Sertoli cells. A human model of the BTB can be established using proliferative human Sertoli cells of the present invention. In the future this could be extended to co-culture models including other testicular cells such as peritubular myoid, Leydig, and germ cells, and could be used to create a model of spermatogenesis.

The model BTB established with human Sertoli cells is used to assess the ability of a model compound, cadmium chloride (Steinberger and Klinefelter 1993; Yu, Sidhu et al. 2005), to affect permeability by measurement of transepithelial electrical resistance (TER). The human BTB model is also used to assess the toxicity of compounds, such the chemotherapeutic agent cisplatin, and the metabolite of the industrial chemical, mono-(2-ethylhexyl) phthalate (MEHP), on the permeability of the cell monolayer and Induction of cell death (Nambu, Kumamoto et al. 1995; Monsees, Franz et al. 2000; Boekelhelde 2005; Yu, Sidhu et al. 2005). Affects on male fertility are a well-established adverse reaction that can occur from treatment with cisplatin [48], and phthalates are industrial chemicals commonly found in many consumer products such as shampoo, cosmetics, and hairspray. [25, 66, 68]. Di-(2-ethylhexyl) phthalate (DEHP) and its active metabolite, mono-(2-ethylhexyl) phthalate (MEHP), cause reproductive toxicity in developing and adult animals.

Flow cytometry is used to analyze the response of the Sertoli cells to the toxins by analysis of the expression by the Sertoli cells of markers for differentiation and for the immunomodulators Fas ligand, TGF-beta1, and the expression of TGF-beta3 that decreases when Sertoli cells form TJ. The expression of the Wilms' tumor gene (WT1) that is switched on in the Sertoli in early fetal life can be used as a stable marker for Sertoli cells against which all other markers is compared. Expression of the Anti-Mullerian hormone (AMH) and cytokeratin 18 are markers for immaturity in the Sertoli cells (Sharpe, McKinnell et al. 2003). The expression of the GATA-1 transcription factor, the p27Kip1 cyclin-dependent kinase inhibitor, and the androgen receptor function are markers for maturation, and the expression of GATA-4 transcription factor and the FSHr are also assessed (Sharpe, McKinnell et al. 2003).

The formation of TJs is determined by (a)transepithelial electrical resistance/or TER, (b) retention of fluid that is assessed by visual inspection, (c) the polarized secretion of transferrin as determined by ELISA (d) and, immunoblots and flow cytometry to determine expression of claudin 3 and 11. The effect on the barrier of supplementation with FSH and testosterone on TJ formation is determined.

To form polarized monolayers with tight junctions human Sertoli cell cultures (passage 1-4) are plated on Matrigel (BD Biosciences, San Jose, Calif.) coated filters in porous 30-mm polycarbonate insert chambers (Millicell PCF; Millipore, Billerica, Mass.) that allow polarized membrane secretions and fit into the wells of a 6-well cell culture plate. Matrigel™ is a solubulized basement membrane preparation extracted from EHS mouse sarcoma. Its major component is laminin, followed by collagen IV, heparan sulfate proteoglycans, and entactin. At room temperature, it polymerizes to produce biologically active matrix material resembling the mammalian cellular basement membrane. Cells are plated at different densities ranging from $0.5$-$5\times10^6$ cells/$cm^2$ to determine the optimum condition for forming tight junctions.

At 1, 4, and 7 days after plating the formation of tight junctions are assessed by filling the apical chamber to a higher level than the basal reservoir and assessing by eye whether equilibrium was obtained within 12 h whereby the meniscus in each reservoir will reach the same level.

Measurement of the TER of the Sertoi cell layers is performed using an impedance meter (Millicell-ERS or Electrical Resistance System) to assess Sertoli cell permeability. The electrical resistance is higher in chambers with impermeable than in permeable cell monolayers. A short (~2 sec) pulse of current (20 μA) is passed through the Sertoli cell epithelia between two sliver-silver chloride electrodes, and resistance is calculated from the change in voltage across the Sertoli cell epithelia. The resistance is multiplied by the effective growth area of the filter to yield the area/resistance (ohms per $cm^2$). To minimize temperature-induced fluctuation when recording TER, cultures are stabilized at room temperature for 0.20 min before TER measurement. A stable TER across the cell layer is evidence of formation of TJs. TER readings are recorded daily. The TER value is calculated by subtracting the mean (n=3) resistance of cell-free Matrigel-covered chambers from resistance measured in the cultures.

The polarized secretion of transferrin is determined by a commercially available sandwich ELISA for transferrin (No. E80-128, Bethyl Laboratories, Montgomery, Tex.). This ELISA has a detection range of 4-250 ng/ml and uses a horseradish peroxidase enzyme conjugate (Onoda, Suarez-Qulan t al. 1990). The ELISA measures the concentration of transferrin and the total amount secreted apically or basally is determined by measuring the total-volume of media in the apical and basal chambers. In a study with rat Sertoli cells, impermeable monolayers produced ratios of secreted transferrin of apical/basal equaling 1.5-2.0. There was little difference between apical and basal concentration of transferrin in permeable layers where the measured ratios of apical/basal were 0.8-1.0.

The effect of supplementation with testosterone (10 µM), and testosterone with FSH (200 ng/ml; both from Sigma) on membrane permeability is determined by measuring TERS and by analysis of the polarized secretion of transferrin. TERs readings are acquired daily for 1 week. Each condition is tested in triplicate and each experiment will be repeated at least twice.

Multicolor flow cytometric analysis using antibodies to the following human proteins when TJs are forming, and after they are formed—at approximately 1 and 4 days post-plating reveals the expression of molecules that are indicative of the maturation and functioning of the TJs and the Sertoli cells. Immunoblots of cell lystates confirm the results of flow cytometry. Antibodies: Claudin-3 (antibody Z23.JM, Invitrogen, Carlsbad, Calif.); Claudin-11 (antibody ZMD.305, Invitrogen); Fas ligand (Nok-1 antibody; BD Biosciences, San Jose, Calif.); TGF-beta1 (antibody 9016.2, Calbiochem, San Diego, Calif.); TGF-beta3 (antibody 236-5.2, Calbiochem); Wilms' tumor gene (WT1, antibody 38-4500, Invitrogen); Anti-Mullerian Hormone (antibody 213816, R & D Systems, Minneapolis, Minn.); Cytokeratin 18 (Chemicon, Temecula, Calif.); GATA-1 transcription factor (antibody E11374, Spring Bioscience, Fremont, Calif.); p27Kip1 cyclin-dependent kinase inhibitor (antibody SPM 348, Spring Bioscience); androgen receptor (antibody 40-6600, Invitrogen); GATA-4 transcription factor (Santa Cruz Biotechnology, Santa Cruz, Calif.); and, follicle stimulating hormone receptor (Biogenesis, Poole, UK).

For single- and multiple-label flow cytometric analysis, Sertoli cells are incubated for 30 min on ice with unconjugated monoclonal antibody against one of the above biomolecules in a total volume of 100 µl of phosphate-buffered saline (PBS) Containing 0.1% bovine serum albumin (BSA). After two washes with PBS-BSA, the cells are incubated for 30 min on ice with 100 µl of the appropriate dilution of anti-antibody to the correct species and immunoglobulin isotype conjugated to a fluorophores such as Alexa 430, fluorescein isothiocyanate (FITC), Texas-Red PE, PE, Cy5PE, Cy7PE, or allophycocyanin (APC). The cells are washed twice with PBS-BSA and then fixed with 1% paraformaldehyde. For analysis of intracellular proteins, the cells are fixed and permeabilized using a kit available from Caltag (Burlingame, Calif.). This facilitates antibody access to intracellular structures and leaves the morphological scatter characteristics of the cells intact, reducing background staining and allowing simultaneous addition of permeabilization medium and fluorochrome-labeled antibodies.

As a control the cells are incubated with an irrelevant antibody from the same species with a matched isotype. Incubation of cells with secondary Ab alone is performed to exclude nonspecific cross-reactivity. The analyses are performed on a FACScan instrument (Becton-Dickinson, San Jose, Calif.) that allows detection of 3 fluorescent colors plus 2 detectors for morphology characterization. The data is analyzed with using CELLQuest Pro 4.1 software (Becton Dickinson).

One set of wells from cultures collected at the same time points as the cells for flow cytometry is used for assessment of transferrin secretion, and one for immunoblots. Cell lysates are obtained by rinsing the cultures with lysis buffer (17 mM MOPS, pH 6.0 with 250 mM sucrose, 25 mM EDTA, 1.0% Triton X-100, 0.2 mg/ml pepstatin A, 1 mM phenylmethylsulfonyl floride, 10 mM dithlothreitol, and 5 mM $MnCl_2$) and incubating at 4° C. for 5 min to burst cells and solubilize membrane proteins. Samples are centrifuged at 15,000×g for 5 min at 4° C. The clear supernatant is collected and used as total cell lysates. For analysis of membrane proteins, the PER Eukaryotic Membrane Protein Extraction Reagent Kit is obtained from Pierce (Rockford, Ill.) and the instructions of the vendor will be followed. This contains a lysis buffer, and two reagents to extract the hydrophobic fraction containing the membrane proteins from the hydrophilic fraction. About 30 minutes and two centrifugations on a benchtop high speed centrifuge (10.000×g) are required.

For immunoblots protein (10-200 µg) derived from Sertoli cell lysates is resolved onto 15% SDS-PAGE gels under reducing conditions. After electrophoresis, the proteins are electroblotted onto nitrocellulose paper and the presence of the proteins of interest is determined using specific primary antibodies and secondary antibodies with detection with the Vectastain ABC (Vector Laboratories, Burlingame, Calif.) kits for protein blots that are available with a choice of three different enzyme detection systems, peroxidase, alkaline phosphatase, and glucose oxidase. The conditions for immunoblots are well known to those who are skilled in the art.

Comparisons are made using multifactorial analysis of variance (ANOVA) taking into account the experimental conditions and different conditions. When more than two conditions are compared ANOVA is used followed by Bonferroni's post hoc analysis. When ANOVA is not used, then the mean±S.D. values are compared by the Student's t test or Mann-Whitney U test and $P<0.05$ is the minimum level of significance.

The effect of cadmium chloride on the model BTB is assessed by measurement of TER. The ability of 200 nM testosterone to protect against and to reverse the effect of cadmium chloride is tested. Cadmium chloride has been shown to damage rat Sertoli cell TJs both in vivo, and in vitro at the 5 and 10 µM concentration (Chung and Cheng 2001). Analysis of the effect of the $CdCl_2$ on rat Sertoli cell TJs showed by assessing DNA levels that the activity was not due to cell toxicity (Chung and Cheng 2001). Treatment with $CdCl_2$ increased the permeability of rodent Sertoli cell monolayers and the effect lasted for a number of days.

$CdCl_2$ at 0.1-10 µm is added to both the basal and apical compartment on approximately days 1 and 4 and incubated for 8 h to assess the effect of $CdCl_2$ on the assembly and maintenance of the inter-Sertoli TJ. Sertoli cells cultured in F12/DMEM or in the presence of media with FSH (100 ng/ml) and 200 nM testosterone, added at day 1 or day 4 are controls. After CdCl2 treatment, all cultures are washed with fresh F12/DMEM three times, and cultures are incubated for an additional 4-7 days. A stable TER across the cell layer is evidence of formation of TJs. TER readings are recorded daily before media is replaced. Each time point has triplicate cultures, and each experiment is repeated at least twice using different batches of cells. Initial studies include wells for analysis of cell death by flow cytometry as described to determine if the $CdCl_2$ is toxic to the cells. Statistical analyses are performed as described above.

The toxicity of two compounds that are known to be toxic to Sertoli cells, the chemotherapeutic agent cisplatin, and the metabolite of an industrial chemical, mono-(2-ethylhexyl) phthalate (MEHP) are quantified and a dose-response curve is constructed. The effect of the compounds on the survival of the Sertoli cells and on the formation and maintenance of TJs assessed by TER as described above also are compared.

In addition, the effect on the expression of Fas ligand is assessed by flow cytometry as Fas ligand on Sertoli cells has been found to be upregulated by MEHP (Lee, Richburg et al. 1999). The percentage of Sertoli cells undergoing apoptotic and necrotic cell death will be assessed by flow cytometry on day 4 and 7. Previous data showed a 15% decrease in viability in immature rat Sertoli cells after 24-h culture in 100 µM cisplatin (Monsees, Franz et al. 2000). Analysis of the effect of 50 100 and 200 µM MEHP on organ cultures of rat fetal and neonatal testes found that there was impaired proliferation of Sertoli cells but no effect on affect early steps of fetal testis formation (Li and Kim 2003).

Sertoli cells are cultured as described above with triplicate cultures for each condition and each experiment is repeated at least twice. The formation of TJs are assessed by visual inspection on days 1, 4, and 7, and polarized secretion of transferrin is analyzed in media harvested on days 1, 4, and 7. Cultures are treated with 1, 10, 100, and 200 µM cisplatin (Sigma, St. Louis, Mo.), or with 1, 10, 100 and 200 µM MEHP (Cambridge Isotope Laboratories, Andover, Mass.) administered for 8 hours to cultures on day 1 or day 4. Flow cytometry is performed as described above on cells harvested on day 1, 4, and 7. An equivalent volume of dimethyl sulfoxide (solvent for MEHP) will be added to cell cultures as a control. The cultures will be washed and fresh media added after the 8-h treatment. Cell death will be assessed in cultures on day 1, 4, and 7.

FACS-based apoptosis assays using Hoechst 33342 and annexin V are used to detect Sertoli cell apoptosis, and incorporation of the intercalating dye propidium iodide (PI) is used to identify necrotic cells as described (Cruz, Frank et al. 2004). Induction of apoptosis for positive controls is performed using 1 µM staurosporine (Sigma). After treatment of the Sertoli cell-BTB models with the compounds in various concentrations as described below, the cells are harvested and flow cytometry is performed on single cell suspensions that are treated with 2 µg/ml PI and 6 µg/ml Hoechst 33342 (Molecular Probes, Inc., Eugene, Oreg.) added 6 min prior to detection. The analysis is performed on a triple laser FACSVantage SE flow cytometer. To detect the bound annexin V, the Sertoli cells are incubated with FITC annexin V in binding buffer (Molecular Probes), according to the manufacturers instructions and analyzed similarly.

The survival of the cells is determined by identifying the population of nonapoptotic and nonnecrotic cells. Gates are established using control populations of cells (prior to induction of apoptosis) that exclude PI and that demonstrate only background levels of annexin V binding or that stain positive for Hoechst 33342 and negative for PI. Apoptotic cells are identified by decreased Hoechst 33342 and increased PI staining or by positive annexin V staining. Statistical analysis is performed as described above.

We claim:

1. A culture of cells, comprising:
   A. a culture surface;
   B. a culture medium disposed adjacent to the culture surface; and
   C. Sertoli cells isolated from normal testicular tissue of an adult human male plated on the culture surface with a cell density $6.25 \times 10^3$ or fewer cells/cm$^2$;
   whereby at least a portion of the plated Sertoli cells are proliferative.

2. A method for establishing a culture of cells, comprising the steps of:
   A. providing a culture surface;
   B. providing a culture medium disposed adjacent to the culture surface;
   C. isolating Sertoli cells from normal testicular tissue of an adult human male; and
   D. plating the cells on the culture surface at a density of $6.25 \times 10^3$ or fewer cells/cm$^2$,
   whereby at least a portion of the adhered Sertoli cells proliferate,
   thereby establishing a culture-expanded population of proliferative Sertoli cells.

3. The method of claim 2 comprising the further steps of
   i. monitoring the culture to detect when confluence of the plated Sertoli cells and Sertoli cells proliferated therefrom, is between 70% and 80%, and
   ii. upon such detection, passaging the culture.

4. The method of claim 3, further including repetitively performing the step of monitoring the culture and the step of passaging of the culture when the detected confluence of Sertoli cells of the passaged culture and Sertoli cells proliferated therefrom, is between 70% and 80%.

* * * * *